US012678232B2

(12) United States Patent (10) Patent No.: US 12,678,232 B2
Zhang et al. (45) Date of Patent: Jul. 14, 2026

(54) SURGICAL SYSTEM

(71) Applicant: Formus Labs Limited, Auckland (NZ)

(72) Inventors: Ju Zhang, Auckland (NZ); Thor Franciscus Besier, Auckland (NZ)

(73) Assignee: Formus Labs Limited, Auckland (NZ)

( * ) Notice: Subject to any disclaimer, the term of this patent is extended or adjusted under 35 U.S.C. 154(b) by 124 days.

(21) Appl. No.: 18/473,326

(22) Filed: Sep. 25, 2023

(65) Prior Publication Data

US 2024/0293182 A1 Sep. 5, 2024

Related U.S. Application Data

(63) Continuation of application No. PCT/NZ2022/050035, filed on Mar. 25, 2022.

(30) Foreign Application Priority Data

Mar. 26, 2021 (NZ) ........................................ 774367

(51) Int. Cl.
*A61B 34/10* (2016.01)
*A61B 5/11* (2006.01)
*G06T 17/00* (2006.01)

(52) U.S. Cl.
CPC ................ *A61B 34/10* (2016.02); *A61B 5/11* (2013.01); *A61B 2034/104* (2016.02); *A61B 2034/105* (2016.02); *A61B 2034/108* (2016.02)

(58) Field of Classification Search
CPC ..... A61B 34/10; A61B 5/11; A61B 2034/104; A61B 2034/105; A61B 2034/108; G06T 7/60; G06T 17/00; G06T 19/20; G06T 2207/30008; G06T 2207/30052; G06T 2219/2004; G06T 2219/2021; G16H 30/00; G16H 50/50
See application file for complete search history.

(56) References Cited

U.S. PATENT DOCUMENTS

2005/0197814 A1 9/2005 Aram et al.
2006/0286522 A1* 12/2006 Ng-Thow-Hing ..... G09B 23/28
482/8

(Continued)

FOREIGN PATENT DOCUMENTS

WO WO 2012/113030 A1 8/2012
WO WO 2013/155501 A1 10/2013
(Continued)

OTHER PUBLICATIONS

Office Action of the corresponding European Application No. 22 776 203.6.
(Continued)

*Primary Examiner* — Brian T Gedeon
(74) *Attorney, Agent, or Firm* — WTA IP Law P.C.

(57) ABSTRACT

In some examples, patient-specific data can be received for a patient's joint. A virtual model of at least part of the patient's joint and associated musculature can be constructed based at least partially on the patient specific data and an implant configuration. A post-operative muscle moment capacity for the patient's joint can be calculated based at least partially on the virtual model. Muscle moment capacity curves and their use to estimate post-operative function are also disclosed.

20 Claims, 10 Drawing Sheets

(56)                     References Cited

U.S. PATENT DOCUMENTS

| | | | |
|---|---|---|---|
| 2008/0221487 A1* | 9/2008 | Zohar ................. | A61B 5/1127 |
| | | | 600/595 |
| 2015/0106024 A1 | 4/2015 | Lightcap et al. | |
| 2018/0008350 A1 | 1/2018 | Varadarajan et al. | |
| 2018/0235762 A1 | 8/2018 | Radermacher et al. | |
| 2020/0219626 A1 | 7/2020 | Otto et al. | |

FOREIGN PATENT DOCUMENTS

| | | | |
|---|---|---|---|
| WO | WO 2018/067966 A1 | 4/2018 | |
| WO | WO 2018/213749 A1 | 11/2018 | |

OTHER PUBLICATIONS

Scott L. Delp et al., An Interactive Graphics-Based Model of the Lower Extremity to Study Orthopaedic Surgical Procedures, IEEE Transactions on Biomedical Engineering, vol. 37, No. 8, Aug. 1990 757-767.
Scott L. Delp et al., Effects of Hip Center Location on the Momentgenerating Capacity of the Muscles, J, Biomechanics vol. 26. No. 4/5. pp. 485.499. 1993. Printed in Great Britain.
International Search Report of PCT application No. PCT/NZ2022/050035 prepared by Australian Patent Office, dated Jun. 20, 2022.

* cited by examiner

Receive patient-specific data for patient's joint    110

Construct a virtual model of at least part of the patient's joint and associated musculature based at least partially on patient-specific data and an implant configuration    120

Calculate a post-operative muscle moment capacity for the patient's joint based at least partially on the virtual model    130

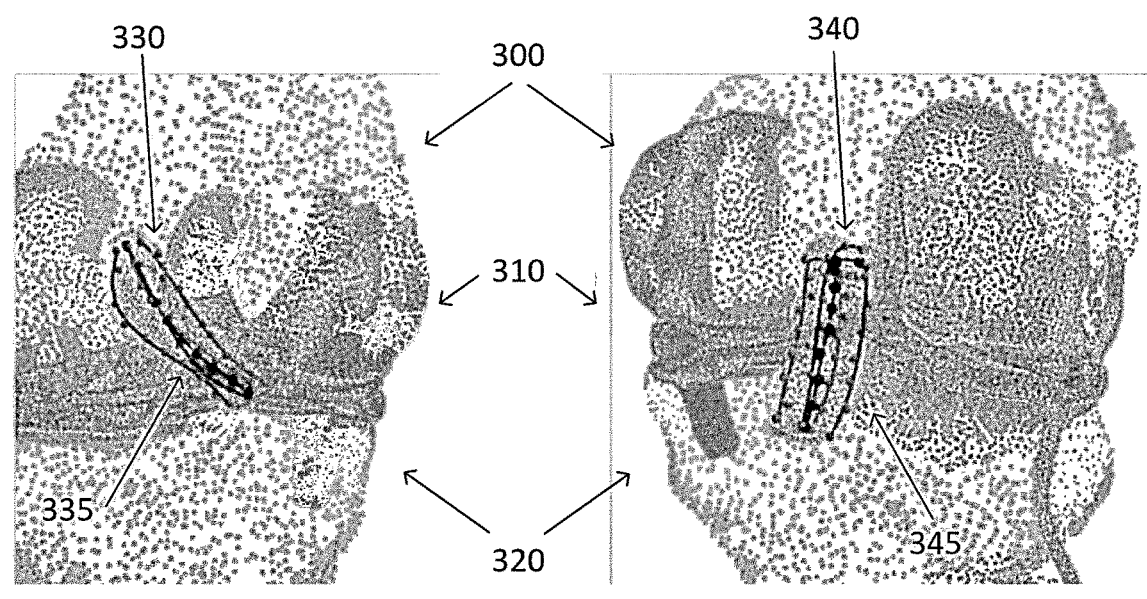
Figure 3A                                        Figure 3B
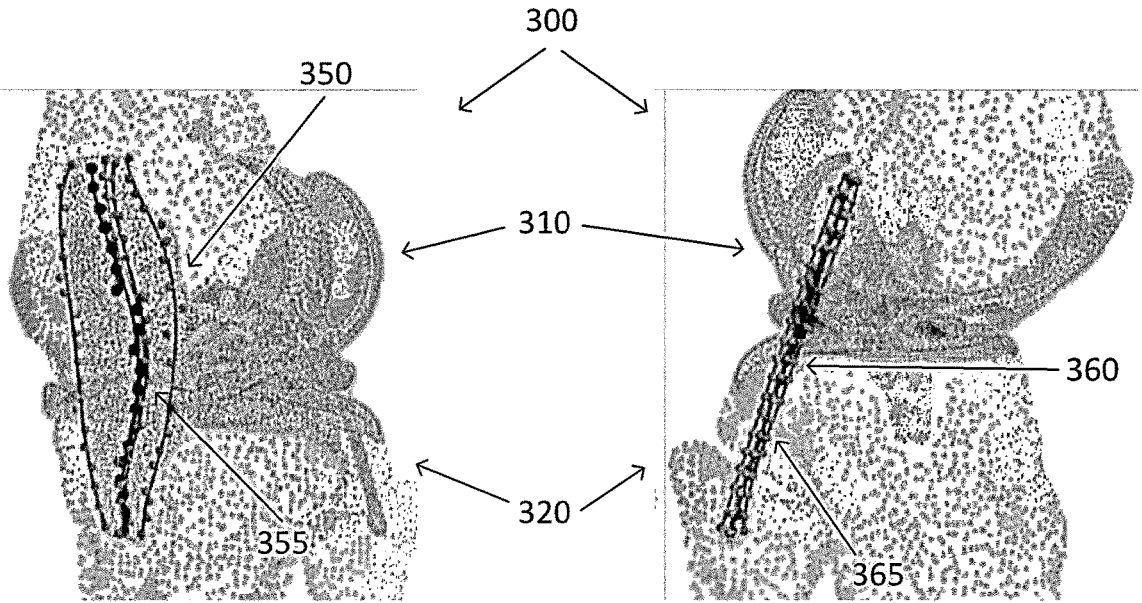
Figure 3C                                        Figure 3D

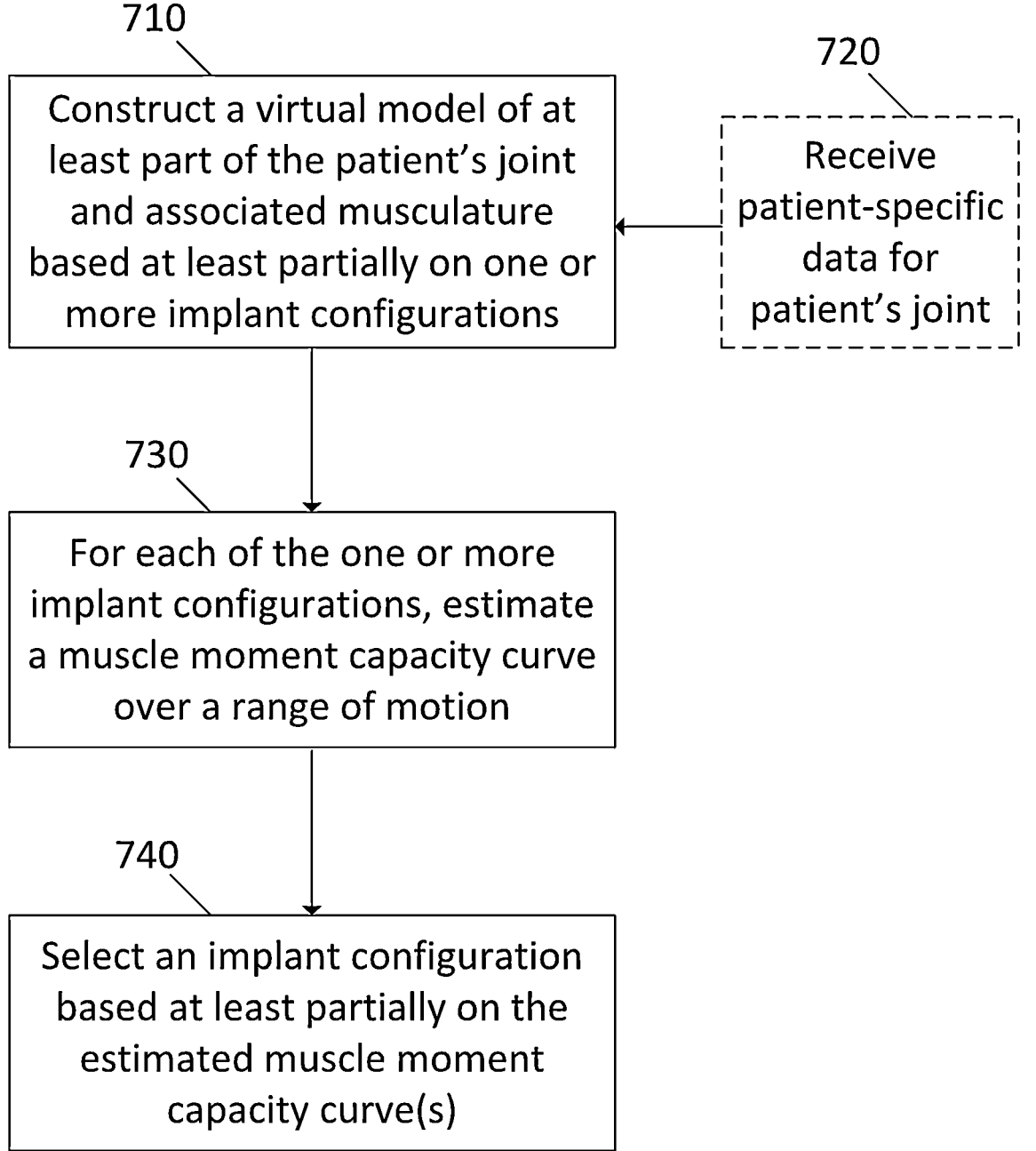

710

Construct a virtual model of at least part of the patient's joint and associated musculature based at least partially on one or more implant configurations

720

Receive patient-specific data for patient's joint

730

For each of the one or more implant configurations, estimate a muscle moment capacity curve over a range of motion

740

Select an implant configuration based at least partially on the estimated muscle moment capacity curve(s)

Receive target post-operative muscle moment capacity curve

920

Compare one or more estimated muscle moment capacity curves against target post-operative muscle moment capacity curve

930

Select an implant configuration based at least partially on the comparison

SURGICAL SYSTEM

CROSS-REFERENCE TO RELATED APPLICATIONS

This is a bypass-continuation application of International PCT Application No. PCT/NZ2022/050035, filed on Mar. 25, 2022, which claims priority to New Zealand Patent Application No. 774367, filed on Mar. 26, 2021, which are incorporated by reference herein in their entirety.

FIELD

This invention relates to systems and methods for estimating post-operative function of joints of patients.

BACKGROUND

Implants can be used to restore or improve the function of joints. The configuration of the implant, such as its position and geometry, can affect the post-operative function of the joint. Changes to the post-operative function of the joint can be patient-specific depending on the patient's geometry, such as the shape and arrangement of the bones of their joint.

SUMMARY

In some configurations, a method of estimating post-operative function of a patient's joint can comprise: receiving patient-specific data for the patient's joint, constructing a virtual model of at least part of the patient's joint and associated musculature, wherein the virtual model is based at least partially on the patient-specific data and an implant configuration, and calculating a post-operative muscle moment capacity for the patient's joint based at least partially on the virtual model.

In some configurations, a method of determining a configuration of an implant can comprise constructing a virtual model of at least part of a patient's joint and associated musculature, wherein the virtual model is based at least partially on one or more implant configurations; for each of the one or more implant configurations, estimating a muscle moment capacity curve over a range of motion using the virtual model; and selecting an implant configuration based at least partially on the estimated muscle moment capacity curve(s).

In some configurations, a method of determining the effect of a surgical procedure on a patient's joint can comprise receiving data of the patient's joint and musculature adjacent to the joint; constructing a virtual model of at least part of the patient's joint and musculature adjacent to the joint using the data; and determining the effect of a surgical procedure on the patient's joint using the virtual model.

In some configurations, a system can comprise at least one processor; and memory storing data instructions that when executed by the at least one processor cause the at least one processor to: receive patient-specific data for a patient's joint; construct a virtual model of at least part of the patient's joint and associated musculature, the virtual model based at least partially on the patient-specific data and an implant configuration; and calculate a post-operative muscle moment capacity for the patient's joint based at least partially on the virtual model.

In some configurations, a system can comprise at least one processor; and memory storing data instructions that when executed by the at least one processor cause the at least one processor to: construct a virtual model of at least part of a patient's joint and associated musculature, wherein the virtual model is based at least partially on one or more implant configurations; for each of the one or more implant configurations, estimate a muscle moment capacity curve over a range of motion using the virtual model; and select an implant configuration based at least partially on the estimated muscle moment capacity curve(s).

In some configurations, a non-transitory computer-readable storage medium can have instructions stored thereon that, when executed by one or more processors of a first computing device, performs the method.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which:

FIGS. 3A-3D depict an example of a virtual model of a joint.

FIG. 7 depicts an example of a method of determining a configuration of an implant.

DETAILED DESCRIPTION

Figure 1:
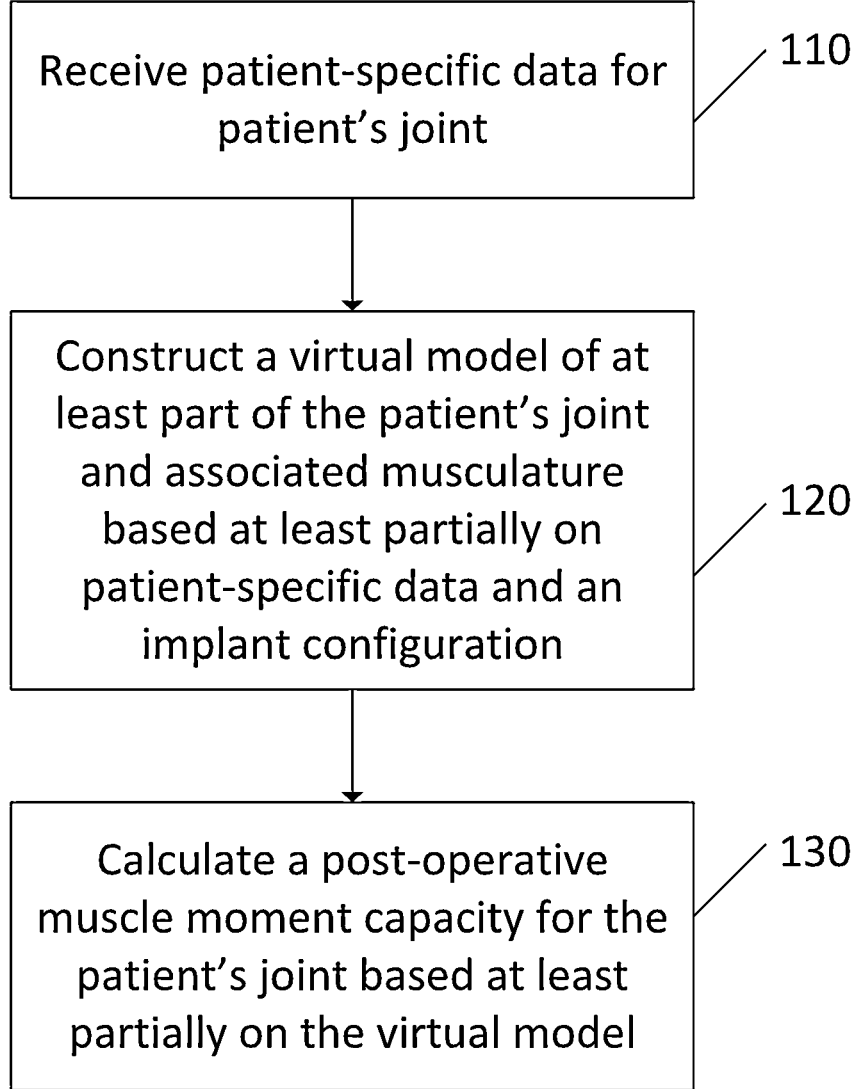
FIG. 1 depicts an example of a method of estimating a post-operative function of a patient's joint.

Implants such as knee or hip replacements can be surgically installed to restore function in their associated joints. The outcome of an implant procedure can depend on the post-operative function of the joint. If the post-operative function of the joint is impaired, the patient may be dissatisfied and may require further surgery to either correct the implant or to restore joint function.

The post-operative function of a patient's joint can depend upon the ability of the musculature associated with that joint to move the joint through its natural range of motion. The contribution of a given muscle to the joint depends on the 'muscle moment capacity', which is a product of the muscle force capacity and the moment arm of the muscle. The moment arm of the muscle depends on the geometry of the joint (e.g. its centre) and the muscle line of action. Similarly, the muscle force capacity can depend upon the geometry of the patient's physiology as changes to muscle lengths or positions can change the force capacity of the muscle. The 'net joint capacity' is the sum of muscle moment capacities and represents the patient's ability to move the joint through its range of motion.

Implant surgeries which affect the geometry of a patient's physiology can therefore affect muscle moment capacities and net joint capacities for the patient's joint, and can therefore affect the post-operative function of the joint. Furthermore, the geometry of the patient's physiology can be patient-specific depending on the geometry of their bones and soft tissues. The changes to the post-operative function of the joint caused by the implant can therefore also be patient-specific.

The approaches discussed herein can be used by clinicians to help estimate the post-operative function of a patient's joint after arthroplasty. The post-operative function may be estimated pre-operatively by simulating the outcome of the arthroplasty on a patient-specific virtual model of the patient's joint. This can help predict whether a given implant will address the patient's needs and can be used as a part of pre-operative planning. Furthermore, implant configurations can be determined or optimised by estimating the post-operative function of a patient's joint. However, the approaches disclosed are not restricted to pre-operative planning and may be used intra-operatively or post-operatively. Furthermore, the approaches disclosed are not restricted to any particular type of arthroplasty and may be used to estimate the post-operative function of ankles, elbows, hips, knees, shoulders, toes, or wrists.

The examples disclosed herein can relate to an improved surgical system. The system may include pre-operative and/or post-operative planning software to simulate or determine the effect of different joint implants or replacements on muscle moment capacity, muscle force capacity, and net joint capacities. The software can simulate or determine how changes to muscle capacity will affect range of motion and/or functional task performance.

The methods and models discussed herein can be implemented by instructions on a computing device, such as an electronic computing device. These can constitute a computer program that is embodied in various media, including tangible or non-tangible media, transitory or non-transitory media and can run on any suitable device. There can also be provided instructions for outputting data to a display device and for producing a user interface (UI) on the computing device or another computing device.

FIG. 1 depicts an example of a method of estimating a post-operative function of a patient's joint.

Patient-specific data for the patient's joint is received at 110. The patient-specific data can include pre-operative images of the patient's joint and/or patient-specific data derived from pre-operative images of the patient's joint, as further discussed herein. The patient-specific data for the patient's joint can also include functional and/or kinetic measurements acquired pre-operatively from the patient, as further described herein.

A virtual model of at least part of the patient's joint and associated musculature is then constructed at 120. The virtual model represents the patient's post-operative joint if an implant were surgically installed in the joint. This can be used to assess the viability or fit of the implant. To this end, the virtual model is based at least partially on the patient-specific data that is received at 110 and also depends at least partially on an implant configuration. The implant configuration represents at least one implant that is being assessed and/or is to be surgically installed in the patient.

The virtual model is then used to at least partially calculate a post-operative muscle moment capacity for the patient's joint at 130, as described herein. A net joint capacity for the patient's joint may additionally or alternatively be calculated. The calculated post-operative muscle moment capacity for the patient's joint may be, for example, displayed to a clinician, used to determine a suitability score for the associated implant configuration, used to provide a recommendation to a clinician, and/or used to determine a pre-operative plan for the implant configuration.

Patient-Specific Data

In some examples, the patient-specific data for the patient's joint that is received at 110 can be at least partially determined using functional and/or kinematic measurements or assessments. These can involve measuring the patient using e.g. wearable force sensors as they perform various movements such as flexion and extension, bending, twisting and common functional movements for that joint. Example functional motions include a regular sit-to-stand motion, more extreme sit-to-stand motion (similar to getting up from a toilet), a deep squat, a golf swing, a stair climb, walking, jogging, or running. Motion capture can also be used to determine patient kinematics and biomechanics, such as muscle velocity. For example, the patient may move their joint through a range of motion while wearing force sensors or while biomechanical forces are measured otherwise. This can be used to build a patient-specific force-velocity profile for one or more muscles associated with that joint. In still further examples, muscle activation information can be determined by measuring muscle activation (e.g. through electromyographic measurements) while the patient performs a functional or kinematic task.

In some examples, the patient-specific data received at 110 can include muscle data such as a muscle length, a muscle volume, a muscle density, a muscle shape, a pennation angle, a line of action of a muscle, and/or a physiological cross-sectional area. The patient-specific data can further include bone data such as a bone geometry, a bone shape, a bone volume, a bone density, an origin of a muscle, and/or an insertion of a muscle. Patient-specific data can also include tendon data such as a tendon length, a tendon size, a tendon cross-sectional area, a tendon shape, a tendon volume, and/or a tendon stiffness. The tendon stiffness may be estimated using a statistical model from tendon image intensity, shape, and volume, plus the size and shapes of the bones and muscles the tendons connect.

The patient-specific data for the patient's joint that is received at 110 can be at least partially determined from one or more pre-operative images of the patient's joint. The pre-operative images can be obtained using one or more radiograph images (e.g. X-ray images), computerised tomography (CT) scans, magnetic resonance imaging (MRI), ultrasound, body surface scans, or other suitable techniques or combinations of techniques. Multiple images can be acquired depicting different areas of the patient's joint and/or a common area from different perspectives. For example, multiple X-ray images can be taken from different angles and/or from different orientations, including neutral orientations. These X-ray images can be combined using stereophotogrammetry to produce three-dimensional image data. Three-dimensional data can also be determined from other imaging techniques using stereophotogrammetry or other applicable techniques.

For example, the patient-specific data received at 110 can be at least partially determined by imaging a muscle of the patient, imaging a bone of the patient, and/or imaging a tendon of the patient. The pre-operative images can be used as a source of geometric data that is at least partially used to create the virtual model of the patient's joint at 120. To this end, the pre-operative images (either alone and/or in combination) typically depict a sufficient portion of the bones of the joint and/or associated musculature (and/or other soft tissues) to create a corresponding virtual model. The geometry can include the size, shape and position of the respective bones, muscles, or other soft tissues, or relevant portions of the bones/soft tissues in three dimensions. The geometry of the bones and/or soft tissues can be determined using several different techniques (or combination(s) of techniques) depending at least partially on the requirements of the virtual model, the imaging techniques used to acquire the pre-operative images. In some examples, at least part of the musculature associated with the joint (or other soft tissues) may be imaged separately to the bones.

In some examples, the bones do not need to be imaged in their entirety depending on the techniques used to construct the virtual model of the patient's joint. For example, if the bones are modelled using statistical shape modelling (as described herein and with reference to FIG. 2), then only a portion of the bones may need to be imaged. For example, if a patient's knee is imaged pre-operatively, then the images (either alone and/or in combination) may only depict the distal femur, tibial plateau, and a proximal portion of the fibula. In other examples, the entirety of the bones (e.g. the entire femur, tibia, and fibula in the case of a knee) can be imaged if required or desired. Similarly, if the musculature associated with the patient's joint is modelled using statistical shape modelling of the bones and scaling (as described herein), then only a portion of the musculature may need to be imaged.

Similarly, pre-operative images do not necessarily need to depict the entirety of all musculatures associated with the joint. In some examples, if the virtual model constructed at 120 will be used to simulate only one functional task or range of motion, then the images may only need to depict the muscles or musculature (or a portion of those muscles/musculature) involved in that functional task or range of motion.

In still further examples, certain muscles associated with the patient's joint may be omitted from the virtual model constructed at 120 depending on their significance and the required fidelity of the virtual model, and therefore may not need to be depicted in the pre-operative images or described in the patient-specific data received at 110. Similarly, it may be acceptable to model only a portion of a given muscle in some examples. In yet still further examples, the data used to model the musculature associated with the patient's joint may not be derived at all from pre-operative images.

Figure 2:
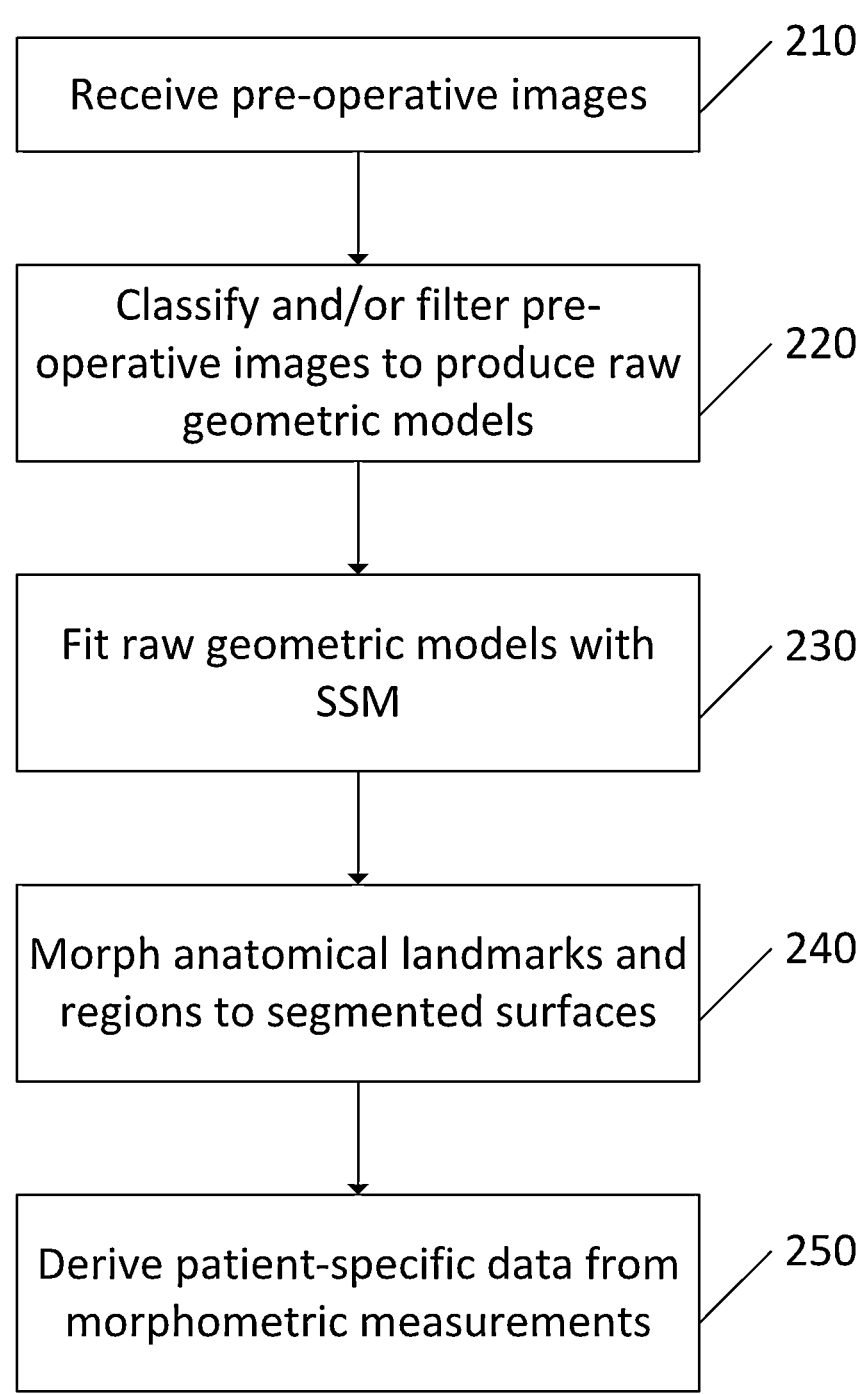
FIG. 2 depicts an example of a method of determining patient-specific data from pre-operative images.

In some examples, at least a portion of the patient-specific data received at 110 is determined by fitting anatomical features derived from one or more pre-operative images using a statistical shape model. FIG. 2 shows an example method of determining patient-specific data from pre-operative images. The pre-operative images are first received by an image processing sub-system at 210, which may be running on a server or computer as described herein. The sub-system can include a trained machine learning model, such as a deep neural network (DNN), and a set of image filters that generate 3D models of bones and/or muscles or soft tissues from the pre-operative images. For example, a DNN can be trained to associate input image texture with output 3D voxel volumes of bones and/or muscles or soft tissues. The sub-system can then apply an image filter or series of image filters to convert the 3D voxel volumes into 3D triangulated meshes. The image filters can include thresholding, region-growing, gaussian smoothing, and marching-cubes.

The pre-operative images received by the image processing sub-system are then classified and/or filtered to produce raw geometric models of anatomical features (e.g. muscles, bones, and other soft tissues) at 220. For example, the image processing sub-system can comprise a DNN trained to automatically segment pre-operative images of the patient's joint based on pixel/voxel intensity or relative greyscale colour (which may be expressed using e.g. Hounsfield units), and/or the intensity and relative greyscale colour of nearby pixels/voxels. Edge detection or similar techniques can be used to generate lines or surfaces that delineate and segment anatomical features (such as separate bones or muscles).

In some examples, the properties of soft tissues (such as muscles and tendons) may be estimated based on sizes, shapes, textures or intensities of the soft tissue that is being measured, in addition to sizes, shapes, textures, or intensities of nearby or adjacent tissues or objects.

Segmented pre-operative images may also be combined to determine 3D representations of anatomical features within the pre-operative images. For example, if multiple segmented pre-operative images are taken from different perspectives, then the segmented images can be combined using stereo photogrammetry to determine 3D voxel volumes of bones and/or muscles or soft tissues. Alternatively or additionally, a clinician or other user can manually segment the pre-operative images. Some approaches may use a combination of automatic and manual segmentation of the pre-operative images.

At 230, statistical shape models (SSM) are used to fit the raw geometric models (e.g. raw triangulated meshes or 3D voxel volumes output by the trained machine learning model and/or manually segmented by a clinician). For example, the SSM can include a mean 3D shape of an anatomical component (e.g. a given bone, muscle, or other soft tissue) measured across a relevant population, alongside a description of the modes of variation of that mean shape observed across the population. The modes of variation can be determined using standard approaches such as principal component analysis. The canonical representation of a given anatomical component described by the SSM can then be fit to the customised raw meshes or 3D voxels derived from the pre-operative images by morphing the mean shape of the anatomical component according to the modes of variation described by the SSM, with each mode of variation weighted by a different score.

For example, the SSM can be fit to a patient's particular anatomical feature by describing the raw 3D representation of the anatomical feature (determined at 220) as a point cloud. The mean shape of the anatomical feature described by the SSM can then be morphed to the point cloud at 230 according to the modes of variation of the SSM by optimising the scores of the modes of variation to minimise a cost function. Example cost functions include the mean squared error and error sum of squares, although other cost functions can alternatively be used. In some instances, this process can produce an approximation of the shape of the patient's anatomical feature that may include non-negligible differences in some regions of the 3D representation. If required, the previously morphed SSM mesh can be further morphed to the anatomical feature by using a finer-scale deformation function to further minimise a cost function. One example of a finer-scale deformation function is a set of radial basis function. In some instances, the final morphed mesh can be within 1 mm RMS of the shape of the individual's anatomical feature.

If the pre-operative images received at 210 and/or raw meshes determined at 220 describe only a portion of the bones comprising the patient's joint (and/or only a portion of at least part of the associated musculature or other soft tissue), then the SSM that is fit at 230 may be fit only to that portion. For example, a 3D representation of a patient's tibial plateau may be determined from radiographic images of a patient's knee. These images may only include a portion of the tibial shaft and may not include the distal portion of the tibia. In this case, the SSM may be fit to the patient's tibia at 230 only with consideration of the 3D representation of the tibial plateau determined at 220. The remainder of the patient's tibia which does not have a 3D representation can then be inferred based on the morphed mesh of the SSM to the 3D representation of the tibial plateau. The end result is a virtual model of the patient's entire tibia which has been derived only from a portion of the tibia. This can be useful for generating whole-bone models or simulations without needing to image the entirety of a given bone. Likewise, entire muscles or collections of soft tissues can be modelled via a SSM using only a 3D representation of a portion of the muscle/soft tissue.

In addition to the mean shape and modes of variation, SSMs for each anatomical feature can also comprise further information about that feature. For example, the SSMs of different bones can include muscle insertions and origin points. Additional information can include information about anatomical points, regions, axes, and other geometric features on the canonical geometry. For example, these can include spheres, cylinders, and/or cones best fitted to the platform.

The SSM for each anatomical feature can also include material properties of the anatomical feature. For example, the stiffness of a tendon can be predicted using an SSM based on the size, shape, and appearance of the tendon, its connected bone, and its connected muscle, as these all may be statistically correlated. This means that mechanical properties of soft tissues or hard tissues can be estimated solely from pre-operative images without requiring physical or mechanical tests.

Once the SSM has been morphed onto the segmented surface of the 3D representation of the patient's bone or soft tissue, the anatomical landmarks and regions on the SSM mean mesh are morphed along to the segmented surface at 240. The morphed mesh is then an accurate representation of the shape of the patient's anatomical feature that is annotated with the locations of the feature's anatomical landmarks, regions, and features. These landmarks, regions, and features provide targets and constraints for the fitting of virtual implants and for the construction of a virtual model of the patient's joint.

Patient-specific data for the patient's joint can then be derived at 250 by taking morphometric measurements of the morphed meshes that are output at 240. In some examples, morphometric measurements may be taken at 230 (e.g. before anatomical landmarks have been assigned.) Patient-specific data may be determined directly using morphometric measurements or patient-specific data may be combined to determine further patient-specific data. For example, once a patient-specific pennation angle for a particular muscle is known alongside a patient-specific volume for the muscle, then a patient-specific physiological cross-sectional area can be determined for that muscle.

In some examples, the patient-specific data derived at 250 can include muscle data such as a muscle length, a muscle volume, a muscle density, a muscle shape, a pennation angle, a line of action of a muscle, and/or a physiological cross-sectional area. The patient-specific data can further include bone data such as a bone geometry, a bone shape, a bone volume, a bone density, an origin of a muscle, and/or an insertion of a muscle. Patient-specific data can also include tendon data such as a tendon length, a tendon size, a tendon cross-sectional area, a tendon shape, a tendon volume, and/or a tendon stiffness.

In other examples, some or all of the above patient-specific data discussed above may be received at 110 without requiring the use of an SSM. For example, the patient-specific data may have been previously determined through analysis of pre-operative images and may be directly provided at 110. In still other examples, the patient-specific data may be derived from pre-operative images without the use of an SSM (e.g. by using raw meshes) if required.

Constructing a Virtual Model of the Joint

With respect to FIG. 1, a virtual model of the patient's joint is constructed at 120 based at least partially on the patient-specific data received at 110 and an implant configuration.

The virtual model constructed at 120 represents a post-surgical model of the patient's joint if a given implant were to be implanted. To this end, the implant configuration upon which the virtual model is at least partially based can correspond to a candidate implant that is being assessed pre-operatively and/or is to be surgically installed in the patient. The implant configuration can influence the geometry of other components within the virtual model of the patient's joint. For example, in the case of a total hip arthroplasty, the position and orientation of the acetabular cup of an implant can affect the position of the centre of the hip, and can therefore affect the position and orientation of the femur with respect to the pelvis. These geometrical changes can be critical in determining how the implant configuration will affect the post-operative function of the patient's joint.

The virtual model constructed at 120 comprises a model of the patient's joint and its associated musculature, which may be modified compared to its pre-operative state by the implant configuration. The virtual model of the joint and its individual components (e.g. modelled bones, muscles, and other soft tissues if present) are articulated and constrained so that the virtual model can be moved through simulated ranges of motion to allow for the calculation of moment arms, muscle moment capacities, and net joint capacities.

Different joints can be modelled as ball-and-socket joints, hinge joints, condyloid joints, pivot joints, gliding joints, and/or saddle joints as appropriate. For example, a shoulder joint can be modelled as a joint with 3 rotational degrees of freedom and 3 translational degrees of freedom; an elbow joint can be modelled as a joint with 1 rotational degree of freedom; a wrist can be modelled as a joint with 3 rotational degrees of freedom; a knee can be modelled as a joint with 1 rotational degree of freedom; an ankle can be modelled as a joint with 3 rotational degrees of freedom; and a hip can be modelled as a joint with 3 rotational degrees of freedom. Other joints may be modelled as appropriate.

Similarly, some joints may be modelled with fewer degrees of freedom if appropriate. For example, if a virtual model is being used to assess the range of motion of a 3-rotational-DoF joint in one rotational plane, then the other two degrees of rotational freedom may be fixed to reduce the complexity of the virtual model and its simulation/calculation.

If a SSM is used to determine the patient-specific data received at 110 (or if the patient-specific data is otherwise annotated to include anatomical landmarks and regions), then the landmarks and regions that are mapped onto the morphed meshes can be used as constraints to determine how the individual components of the model are arranged with respect to one another and to determine their relative degrees of freedom. In other examples where a SSM is not used, then a rules-based approach can be used to determine how constituent elements of the virtual model are arranged. Alternatively, a user (e.g. clinician) may define anatomical landmarks and/or axes of rotations of joints to construct the virtual model.

The implant configuration used in the construction of the virtual model can comprise information about the implant itself (such as its type, geometry, and size), and information describing how the implant is oriented or arranged within the virtual model (e.g. its position and inclination/attitude). For example, the implant configuration can comprise:

- an implant type, an implant size, an implant 3D position, an implant 3D orientation, and/or an implant material;
- a femoral stem size, a femoral stem 3D position, a femoral stem 3D orientation, a femoral stem neck angle, a femoral stem material, and/or a femoral stem neck offset
- a femoral head size, a femoral head 3D position when attached to a femoral stem, a femoral head material, and/or a femoral head offset along a femoral stem neck when attached to a femoral stem;
- an acetabular cup size, an acetabular cup shape, an acetabular cup 3D position, an acetabular cup 3D orientation, an acetabular cup material, and/or an acetabular cup thickness;
- an acetabular cup liner size, an acetabular cup line shape, an acetabular cup liner thickness, an acetabular cup liner articulation (e.g. solid or articulated), and/or an acetabular cup liner material.

All of these implant characteristics can have an influence on the position and orientation of joint components relative to one another (e.g. the position and orientation of the femur relative to the pelvis and the centre of joint rotation), and therefore can affect muscle moment capacities and net joint capacities.

Although several of these characteristics relate to implants used in hip arthroplasties, other implant parameters or characteristics can also be included in the implant configuration depending on the application of the implant. For example, if the implant is used in a total knee replacement or a uni-compartmental knee replacement, then the implant configuration can include implant characteristics specifically related to knee replacements. Similarly, if the implant is used in an anatomical or reverse shoulder replacement, then the implant configuration can include implant characteristics specifically related to shoulder replacements.

In some examples, the implant configuration can be implemented into the virtual model using a library of implant shapes, sizes, and other implant parameters. If the constituent components of the virtual model of the patient's joint include annotated landmarks or anatomical regions (provided by e.g. a SSM used to fit raw meshes), then the landmarks and anatomical regions mapped onto the morphed meshes can be used as constraints to determine how the implant fits into or onto the associated bone or within the virtual model of the patient's joint.

In some examples, a virtual pre-operative model of the patient without an implant configuration can be created using patient-specific data, and the pre-operative model can then be modified to comprise the implant configuration. In these instances, the first virtual model of the patient's joint can represent the joint as it is pre-operatively, and the modified virtual model can correspond to a simulated surgery to install an implant according to the implant configuration. In other examples, the virtual model may be constructed comprising an implant configuration in the first instance.

The extent of patient-specific data used to construct the virtual model at 120 can vary. In some examples, all the constituent components of the virtual model (such as the bones of the joint and its associated musculature and other soft tissues) can be derived from patient-specific data. In other examples, only some of the constituent components of the virtual model may be derived from patient-specific data, and other components (such as some bones or some muscles) may be derived from other sources. For example, the virtual model may include one or more generic components such as bones or muscles that are not patient-specific. In some examples, these can be derived from statistical averages of populations that correspond with the patient (such as age, ethnicity, height, weight, nationality, etc.)

In still further examples, parts of the virtual model may be constructed using a combination of patient-specific data and non-patient-specific data. For example, a muscle of the virtual model may be at based on a patient-specific muscle volume and muscle size that was derived through analysis of pre-operative images. The modelled muscle may be given a pennation angle that is determined using literature values or other empirical measurements that are not specific to the patient. The physiological cross-sectional area of the modelled muscle may then be determined using a combination of the patient-specific volume/size and the non-patient-specific pennation angle.

In some examples, the virtual model constructed at 120 may comprise a Hill-type representation of a muscle. In these examples, the modelled muscle (and/or tendon) may not include a volume, and may instead be approximated by one or more line segments corresponding to lines of action of the muscle. The Hill-type representation of the muscle may still be informed using patient-specific data (such as muscle-fibre lengths and activation levels), but its behaviour (such as its force-length relationship) may be determined using a Hill-type approach. In some examples, a Hill-type representation of a muscle can be determined by identifying a plurality of lines of action of a muscle and summing the plurality of lines of action to determine a collective representation of a moment of the muscle.

In other examples, the virtual model constructed at 120 may comprise a volumetric representation of a muscle. In these examples, the muscles of the virtual joint may have a definite volume within the virtual joint, and may be computationally simulated accordingly (for example, by simulating contact with other 3D surfaces defined within the virtual model.) The volumetric representation of the muscle may be determined using patient-specific data, such as muscle shape and muscle volume, to model the patient's muscles with a higher fidelity. The behaviour of the volumetric representation of the muscle may not be determined using a Hill-type approach, and may instead be determined using more complex simulations as described herein.

In still further examples, the virtual model constructed at 120 may comprise a combination of Hill-type representations of muscles and volumetric representations of muscles. This may be advantageous where some muscles are particularly significant muscles and benefit from the higher fidelity of volumetric modelling, whereas less significant muscles can be modelled using Hill-type representations to reduce the computational complexity of the model. Similarly, it can be advantageous to model muscles with complicated architecture or with complex wrapping around bones volumetrically rather than using line segments.

In some examples, one or more of the muscles of the virtual model may be wrapped around a bone, portions of a bone, or other anatomical feature within the virtual model. If the muscle is modelled using a Hill-type representation, then the muscle path may be defined as a plurality of line segments drawn between a plurality of wrapping points. The wrapping points may be determined from patient-specific data (such as pre-operative images indicating where the muscle wraps about the bone) or may be determined using reference or literature wrapping points. In some examples, morphed meshes fit by a SSM can include muscle wrapping points. If the muscle is represented volumetrically, then the muscle can be wrapped about the bone or other anatomical feature by accounting for the contact between muscles within the virtual model. For example, contact between the surface of the muscle and other surfaces within the virtual model can be simulated to delineate the muscle in question from its surrounding anatomy and to determine wrapping points with respect to a bone. Contacts between muscles and adjacent soft or hard tissues can be resolved using contact mechanics.

The end result of the model construction process is an articulated virtual model of the patient's joint that is based at least partially on patient-specific data. The virtual model can allow for relative motion of components of the joint so that the biomechanics of the patient's joint can be assessed virtually. The virtual model also incorporates an implant configuration for the patient's joint and models the corresponding changes to the patient's physiology, such as geometric changes between bones and muscles of the patient. This allows for the simulation of muscle and joint forces and to assess the implant configuration on the patient in a patient-specific way. In particular, the virtual model can be used to calculate muscle moment capacities for the joint and a net joint capacity.

FIGS. 3A-3D depict an example virtual model 300 of a patient's knee from different perspectives. The virtual model includes a modelled proximal tibia 310 and a distal femur 320. The four main ligaments of the knee, the ACL, PCL, MCL, and LCL are represented by volumes 330, 340, 350, and 360, respectively. These volumetric ligaments and bones have been determined using patient-specific data. Multiple lines of action 335, 345, 355, and 365 can be calculated for each volumetric representation, as illustrated by the solid lines within each volume, or the entire ligament can be represented within a finite element analysis, as described herein.

Simulation and Calculation of Muscle Moment Capacities

With respect to FIG. 1, the post-operative function of the patient's joint is estimated by calculating a post-operative muscle moment capacity for the patient's joint at 130. This calculation is based at least partially on the virtual model of the patient's joint that is constructed at 120.

A muscle moment capacity is a measure of the capacity of a muscle to exert the moments required to rotate or move the patient's joint through the range of motion of the patient's joint. The muscle moment capacity of a given muscle therefore depends on the type of joint and its associated motion. The post-operative function of the patient's joint can be estimated by calculating muscle moment capacities for a plurality of muscles for the joint, as the motion of a given joint will typically involve a plurality of muscles. Estimating the post-operative function of the patient's joint can help the clinician determine how an implant configuration will affect the patient's joint through surgery and can be used to assess the suitability of a given implant configuration.

To this end, the virtual model of the patient's joint that is constructed at 120 is used to simulate the range of motion for the patient's joint and to calculate at least one muscle moment capacity for the patient's joint. The type of motion or range of motion can vary depending on what joint is being modelled, what implant is being assessed, and the specific type of motion under consideration. For example, the range of motion may be rotation, flexion, or abduction about one or more axes. For example, the range of motion may be simple flexion about a single axis, or may be internal rotation about an axis at 90 degrees flexion.

In other examples, the simulated motion may be a more complex functional movement that involves rotations and/or translations about multiple degrees of freedom. Example functional motions include a regular sit-to-stand motion, more extreme sit-to-stand motion (similar to getting up from a toilet), a deep squat, a golf swing, a stair climb, walking, jogging, or running. The paths of motion used to determine the simulated movement may be derived from patient-specific data (such as motion capture of the patient performing a given functional task) or may be derived from a generic kinematic movement mapped on to the virtual model of the patient's joint. If a generic kinematic movement is used to simulate the motion, then the kinematic moment may be scaled accordingly to the patient's physiology.

The muscle moment capacity for a given muscle is defined as the product of a moment arm of the muscle and the muscle's force capacity:

$$M_{MC} = ma \times F_M$$

where $M_{MC}$ is the muscle moment capacity, ma is the moment arm for the muscle, and $F_M$ is the muscle force capacity.

The moment arm ma and muscle force capacity $F_M$ are both affected by the geometry of the patient's joint. An implant configuration which alters the geometry of the patient's joint can therefore alter the value of the moment arm ma, the muscle force capacity $F_M$, and/or the muscle moment capacity $M_{MC}$.

Figure 4:
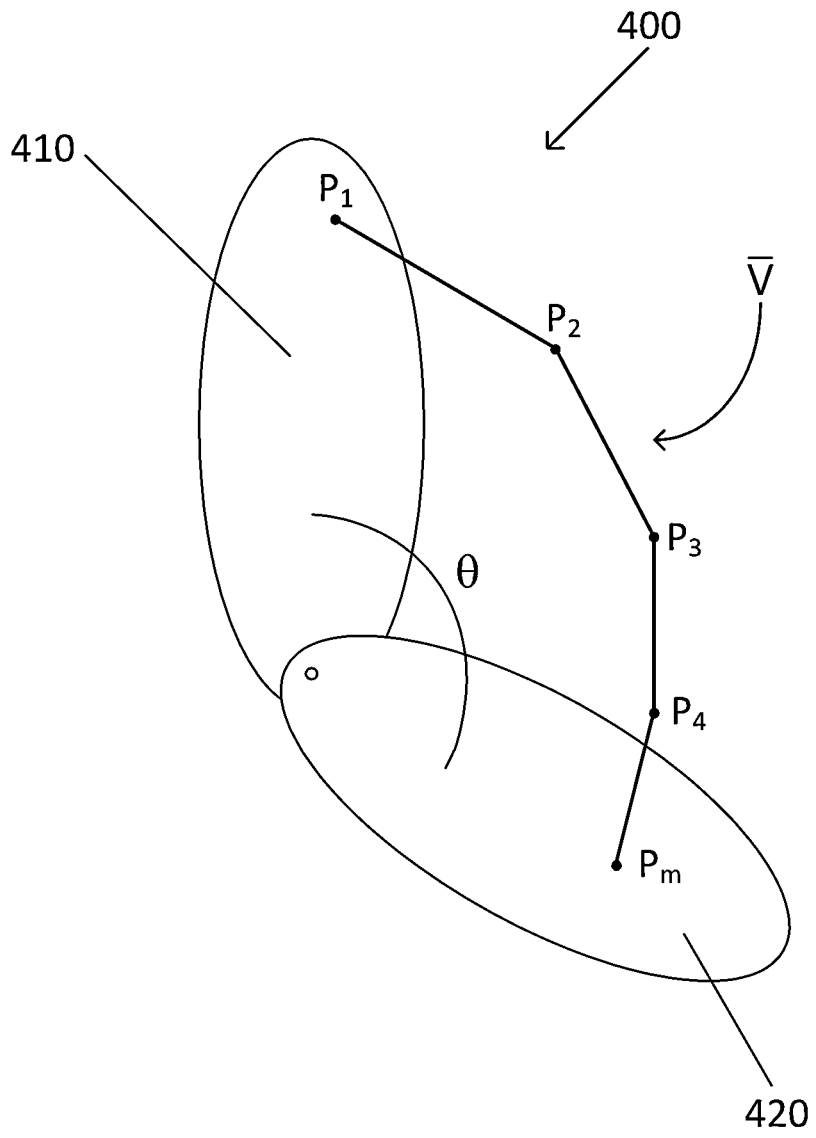
FIG. 4 depicts an example revolute joint.

The moment arm ma can be mathematically determined using several techniques. In some examples, the moment arm ma can be determined over a range of motion by considering changes in muscle length with respect to changes in the angle of a joint. FIG. 4 depicts an example revolute joint 400 (highly stylised for the sake of illustration) which traverses an arc $\theta$ over a range of motion. A muscle crosses the two components 410 and 420 and traverses a path $\nabla$ as the two components 410 and 420 rotate with respect to one another. The path $\nabla$ can be represented as a segment of linear line segments defined by a set of coordinates $P_1, P_2, \ldots, P_m$. The moment arm can then be defined as $$ma = \frac{\partial l}{\partial \theta}$$

where l is defined as $|\nabla|$. If the joint is involved in rotation about more than one axis, then the moment arm can be defined by taking the derivative or partial derivative with respect to the range of motion about that axis.

In other examples, the moment arm ma can be determined by taking the perpendicular distance of a line of action of the muscle to the joint centre.

For Hill-type muscle representations, the muscles can be represented using line segments. The change in muscle length with respect to the range of motion can be determined by simulating movement of the virtual model across the relevant range of motion and then calculating $$\frac{\partial l}{\partial \theta}$$

(and/or other partial derivatives if rotation about multiple axes are involved.) This technique is sometimes referred to as the 'tendon excursion method'. The value of the moment arm will therefore depend at least partially on the range of motion used in the simulation. Alternatively, a line segment of the Hill-type muscle can correspond to the line of action of the muscle and can be used to determine the perpendicular distance from the muscle line of action to the centre of the joint (as depicted in FIG. 5, 530).

For volumetric representations of muscles, in some examples, a single line of action can be ascribed to the muscle by simulating characteristics of the muscle (such as pennation angles and the muscle's longitudinal axis.) This line of action can be used to calculate a moment arm ma for the muscle. Alternatively, multiple lines of action can be determined or a finite element method can be used to solve the mechanics of the muscle throughout a range of motion. This net line of action can be used to determine a net moment arm ma for the muscle.

In still further examples, a more complex calculation of the moment arm ma for a volumetric representation of a muscle can be performed. For example, a finite element analysis can be used to simulate a deformation of the 3D volumetric representation of the muscle through the range of motion of the virtual model of the patient's joint. In some examples, finite element analysis is used to simulate the change in muscle fibre lengths as a function of joint angle as the joint moves through its simulated motion.

Figure 5:
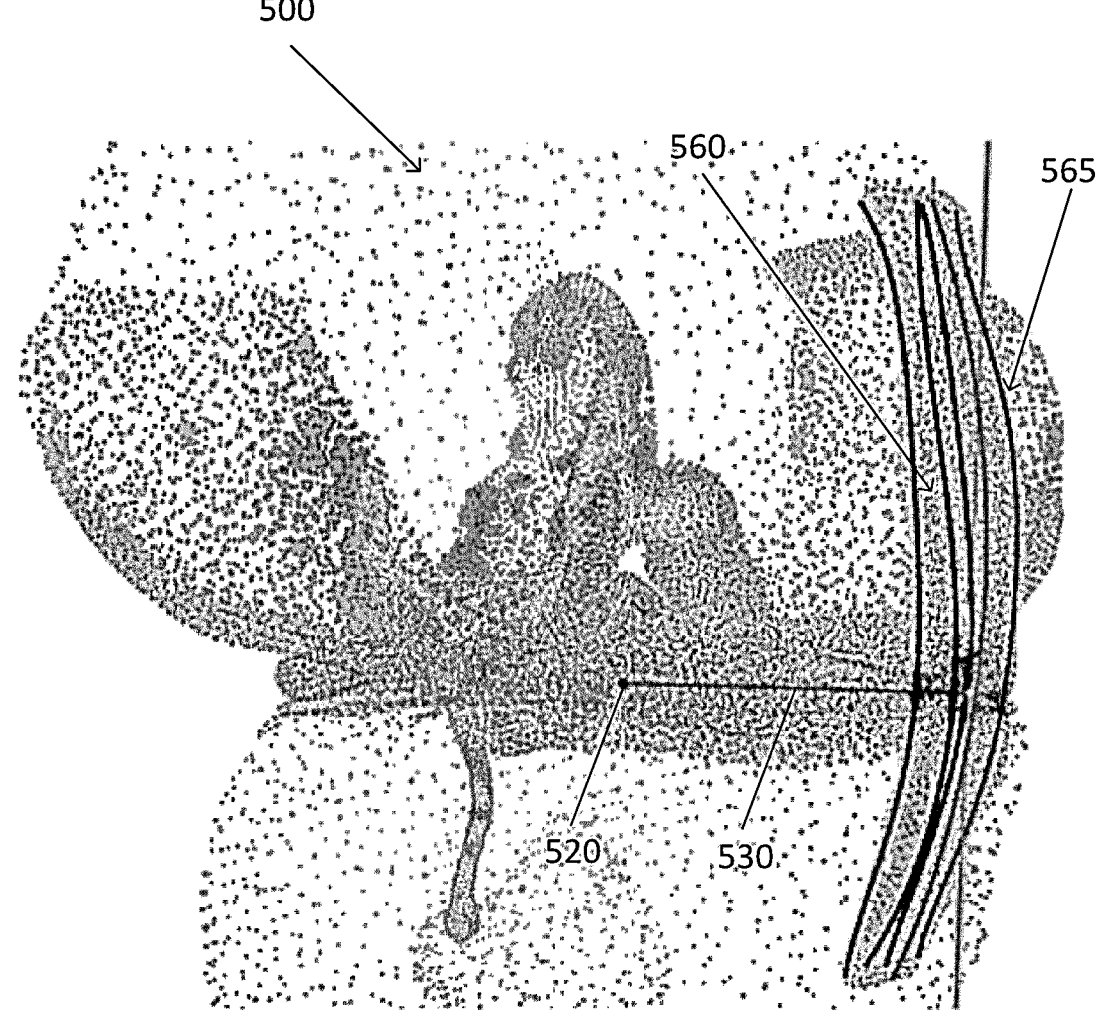
FIG. 5 depicts an example of a virtual model of a joint.

FIG. 5 depicts the calculation of a moment arm using the virtual model 500 of a patient-specific knee depicted in FIGS. 3A-3D. The moment arm has been calculated for the lateral collateral ligament (LCL) 560 by measuring the deformation of the volumetric representation of the LCL ligament 560 via finite element analysis. The lines of action 565 that are depicted were calculated similarly. The centre 520 of the knee joint is indicated and can be seen to correspond with the perpendicular distance 530 from the lines of action 555 of the ligament 560 to the centre of rotation in the plane of interest 520.

The muscle force capacity, $F_M$, is the capacity of the muscle to produce a force. The muscle force capacity $F_M$ can be a function of muscle size, muscle length, muscle velocity, and muscle activation. Some or all of these characteristics can be informed entirely or partially by patient-specific data that is received (with respect to FIG. 1) at 110.

For example, muscle sizes and lengths may be determined through analysis of pre-operative imaging, as has been described. For example, the muscle size can be estimated using physiological cross-sectional area. The physiological cross-sectional area can be estimated as a ratio of the muscle volume to fibre length, which may be determined using patient-specific data. Muscle activation can be determined, for example, using electromyographic measurements of the patient to provide relative activation of the muscles or muscle groups. In other examples, a combination of patient-specific data and non-patient-specific data may be used.

For Hill-type muscle representations, the muscle force as function of length can be determined using a Hill-type force-length relationship based on passive and active components. The Hill-type force-length relationship may be determined using the underlying patient-specific data (e.g. a patient-specific muscle resting length) which underpins the modelled Hill-type representation of the muscle. In some examples, the Hill-type force-length relationship can be determined using a scaled representations a force-length relationships as cubic splines and can be interpolated based on muscle activation, which may be patient-specific.

Similarly, a force-velocity relationship for a given muscle can be determined using a Hill-type force-velocity relationship. The Hill-type force-velocity relationship may also be determined using a scaled representation of a force-velocity relationship using cubic splines and may also be interpolated based on activation, which may be patient-specific data. Alternatively or additionally, a force-velocity relationship for a muscle can be determined from patient-specific data (for example, using motion capture and wearable sensors, gait analysis, etc, as has been described previously) The force-length-velocity relationships can be represented as splines (e.g. cubic or quintic) and scaled to match patient-specific or population data and interpolated as a function of activation.

For volumetric representations of muscles, the muscle force capacity $F_M$ can be determined using more complex finite element analysis. For example, a change in muscle fibre length as a function of joint angle can be volumetrically simulated as the virtual model of the patient's joint is simulated through its range of motion. In some examples, the simulation can be performed using continuum mechanics. The force-length relationship of the volumetric representation of the muscle can then be accounted for by modelling the muscle using a constitutive model. Similarly, more complex finite element analysis techniques can be used to simulate or determine force-velocity relationships for volumetric representations of muscles. Alternatively, force-velocity relationships can be determined for volumetric representations of muscles using patient-specific data, as has been described.

Once the moment arm ma and muscle force capacity $F_M$ have been calculated for a given muscle of the patient's joint, the muscle moment capacity $M_{MC}$ can then be calculated to estimate post-operative function of the patient's joint. The muscle moment capacity $M_{MC}$ can be calculated at different points in the range of motion of the virtual model of the patient's joint by multiplying the muscle force capacity $F_M$ at that point in the range of motion with the moment arm ma of the muscle at that point. A plurality of muscle moment arms, muscle force capacities, and muscle moment capacities can be calculated for a plurality of muscles associated with the patient's joint if multiple muscles are used in the motion of the joint.

Figure 6:
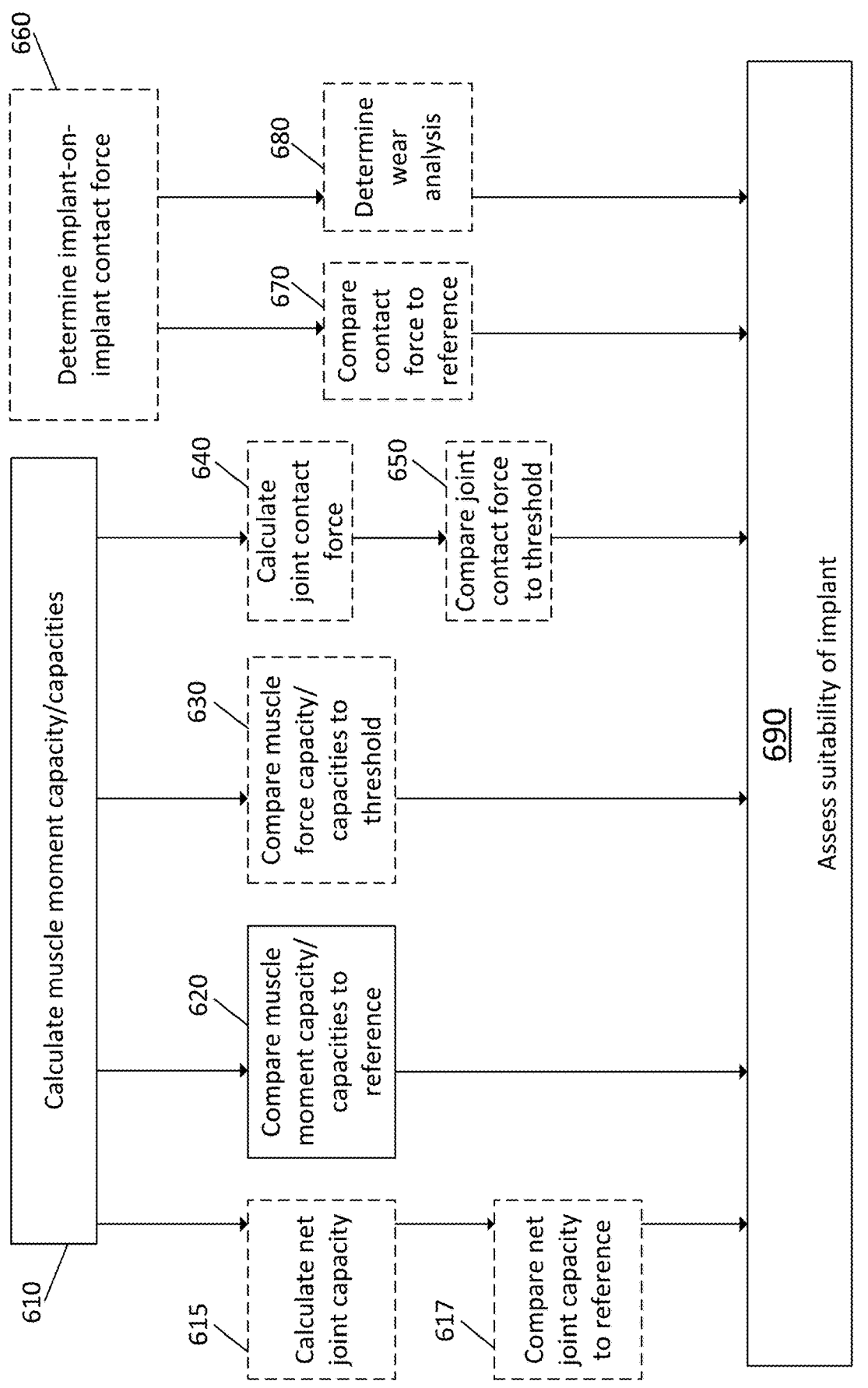
FIG. 6 depicts an example of a method of assessing post-operative function of a joint.

FIG. 6 depicts an example method of assessing the post-operative functionality of the patient's joint. The muscle moment capacity (and/or muscle moment capacities and/or net joint capacity) is calculated at 610 as has been described, and may be calculated continuously throughout the range of motion of the joint. To assess the post-operative functionality of the patient's joint, the calculated muscle moment capacity or capacities is/are compared against a reference muscle moment capacity (such as a lower threshold) required to move the joint throughout its range of motion at 620. In some examples, the reference muscle moment capacity may be derived from an external source (e.g. medical literature) and may be scaled with respect to the product of the patient's height and mass. In other examples, a reference muscle moment capacity may be determined using patient-specific data such as data derived from motion capture. If multiple muscle moment capacities are calculated at 610, then each calculated capacity may be compared against a different reference as required. Similarly, the value of the reference may change as the virtual model of the joint traverses through its simulated range of motion.

The suitability of the implant configuration is then assessed at 690 based at least partially on the comparison at 620. If the comparison at 620 suggests that the muscle moment capacity is below the reference muscle moment capacity, then the simulated virtual model of the patient's joint may suggest that the implant configuration that is being assessed is unsuitable for patient. For example, the implant configuration may have reduced the muscle force capacity of the muscle (by e.g. changing a resting length of the muscle, or otherwise affecting the length-force relationship of the muscle), or may have reduced the moment arm of the muscle (by e.g. changing the centre of rotation of the joint based on the implant location). Alternatively, the implant configuration may not have reduced the moment arm or its force capacity, but may have failed to increase the muscle force capacity/moment arm to the point where it remains insufficient to move the joint through its full range of motion.

In some examples, the assessment of the implant configuration at 690 may produce a binary outcome, e.g., 'suitable' or 'unsuitable'. In other examples, the outcome of the assessment may be a score that indicates or quantifies suitability. The score can have multiple dimensions representing different characteristics of the implant configuration; for example, the implant configuration may have separate scores for implant fit, implant longevity, restoration of post-operative function, etc.

In some examples, the implant configuration may be considered unsuitable at 690 if the calculated muscle moment capacity is below the reference used in the comparison at 620. If multiple muscle moment capacities are calculated to estimate the post-operative function for the patient's joint, the implant configuration may be considered unsuitable if any single muscle moment capacity fails the comparison at 620. In other examples, each muscle moment capacity may be scored depending on its deviation from the reference used at 620 and the suitability of the implant configuration may be determined by considering the net score for the joint. In some examples, the scores of different muscle moment capacities can be weighted depending on their contribution to the movement of the joint.

In addition to estimating post-operative function by comparing one or more muscle moment capacities (and/or net joint capacity) to a minimum threshold or value, the post-operative function of the patient's joint can be estimated by comparing one more calculated muscle force capacities to a maximum threshold or value at 630. As has been described, the muscle moment capacity is given as the product of the muscle force capacity multiplied by the moment arm of the muscle. Some implant configurations could dramatically increase the muscle force capacity (e.g. by altering muscle a length and thereby changing its force-length relationship)

whilst decreasing the moment arm of the muscle. The muscle moment capacity may only change slightly (if at all) as it is the product of these two numbers, but the muscle force capacity could lead to dangerous or undesired biomechanics or post-surgical outcomes. For example, if the implant configuration increases the muscle force capacity to an excessive level, the muscle may tear, damage bones/tendons, damage the implant, or cause other problems.

To this end, a muscle force capacity calculated from the virtual model of the patient's joint can be compared against a threshold at 630. The threshold can be determined using patient-specific data, or alternatively may be an external reference (for example, based on a literature value). The threshold may be scaled to the patient, for example by scaling with the product of the patient's height and mass. The assessment of the suitability of the implant configuration at 690 can then based at least partially on the comparison at 630. The implant configuration may be considered unsuitable at 690 if the calculated muscle force capacity (or any one of the plurality of muscle force capacities) is above the threshold. Alternatively, the muscle force capacity/capacities can be scored and weighted to assess the implant configuration.

In some examples, the post-operative function of the patient's joint may further be estimated by calculating a joint contact force at 640. The joint contact force is based at least partially on the muscle moment capacity and the virtual model of the patient's joint. The joint contact force can correspond to a force at an interface between an implant and bone and can highlight conditions that could cause damage to the bones or to the implant. The joint contact force can then be provided to the clinician to help assess the viability of the implant configuration/post-operative function of the patient's joint or can be assessed against a reference.

For example, a net force or average force that the implant experiences (or the bone/implant interface) can be determined over the range of motion of the joint. These forces may be compared to a threshold (such as an upper threshold) at 650 to determine potentially excessive forces and the comparison can be used to at least partially determine the suitability of the implant configuration at 690. In other examples, more complex finite element analysis can be performed to calculate forces across different regions of the implant and/or the implant/bone interface, and these forces can be used to assess the suitability of the implant configuration at 690. This approach can detect and highlight areas where the patient's bone may be overloaded and could fracture. Specific vectors or portions of the force may also be calculated. For example, a shear component of the force may be calculated and used to predict whether dislocation may occur.

Similarly, the joint contact force calculated at 640 can be compared against a lower threshold at 650 to detect areas where the patient's bone may be underloaded and therefore could lead to bone loss in the future. These regions can be highlighted to the clinician and can also be used to determine the post-operative functionality of the joint, and optionally can be used to determine or optimise an implant parameter for the patient's joint. The comparisons at 650 can then be used to assess the suitability of the implant configuration at 690. In some examples, if the comparison at 650 suggests that the determined forces are too high or are too low in general or in particular areas of the implant, the implant configuration can be deemed unsuitable at 690. In other examples, the joint contact forces and/or the outcome of their comparisons can be scored and/or weighted to assess the implant suitability at 690.

In still further examples, estimating the post-operative function of the patient's joint can comprise determining an implant-on-implant contact force at 660. For example, implant-on-implant contact forces can be determined based on equal and opposite reactions to muscle forces and/or through a finite element analysis of different components of the implant as the virtual model of the joint is moved through its range of motion. The implant-on-implant contact forces can be compared against a reference at 670 used to indicate excessive implant-on-implant forces and to assess the suitability of the implant configuration at 690.

The implant-on-implant contact forces that are optionally calculated at 660 can also be used to determine wear analysis for the implant at 680. The wear analysis can indicate how the implant may wear over time if it were implanted into the patient. For example, a relationship between the average implant-on-implant force and the average lifetime of the implant can be used to estimate the wear of the implant for the patient. This information can be provided to the clinician to help determine the suitability of the implant at 690 and to determine the function of the patient's post-operative joint.

In some examples, the post-operative function of the patient's joint can further be estimated by calculating a post-operative net joint capacity at 615 at least partially on the post-operative muscle moment capacity. The net joint capacity, $J_{NC}$, is the sum of all muscle moment capacities that are used to move the joint throughout its range of motion:

$$J_{NC} = \Sigma M_{MC}$$

The net joint capacity $J_{NC}$ represents the net capacity of the joint required to move the entire joint through its range of motion, such as an ambulatory task. This can be a useful metric accompanying the muscle moment capacity. The net joint capacity may be compared to a reference value (e.g. a lower threshold) at 617 to estimate post-operative function of the joint and to determine whether the joint has a sufficient capacity to move through its range of motion. This may also be scaled to the patient. The comparison used at 617 can then be used to help assess the suitability of the implant configuration at 690.

In some examples, the post-operative muscle moment capacity for the patient's joint (calculated at 130 with respect to FIG. 1) and/or the suitability of the implant (determined at 690 with respect to FIG. 6) can be used to inform or assess a surgery. For example, the calculated muscle moment capacity and/or determined suitability can be displayed to a clinician on, e.g., a monitor or other display device. The clinician can then use this information to assess whether an implant configuration is suitable for a given patient and a given operation.

In some examples, a suitability score may be determined for the implant configuration using the calculated muscle moment capacity and/or suitability of the implant and may be provided (e.g. displayed or outputted) to a clinician. For example, the suitability score can be a quantitative score assessing the suitability of the implant. In some examples, the suitability score may be a single quantitative number representing the entire implant configuration. In other examples, the suitability score may have multiple dimensions. For example, a certain characteristic of the implant configuration (such as a material of the implant) may be given a score, while other characteristics of the implant configuration (such as the position/orientation of the implant) may be given a different score. In still further examples, the single-dimensional or multi-dimensional suitability score may be qualitative (e.g. very unsuitable, unsuitable, suitable, very suitable) instead of quantitative.

In still further examples, the clinician may be provided with a recommendation based at least partially on the calculated muscle moment capacity and/or determined suitability of the implant. For example, a system can recommend that some component of the implant configuration (such as the implant position/orientation) should be altered to better improve the post-operative function of the patient's joint based at least partially on the calculated muscle moment capacity and/or determined suitability of the implant. In still further examples, the system may recommend an entirely different implant configuration given the muscle moment capacity/implant suitability.

In some examples, a pre-operative plan can be determined for the patient and the implant configuration. For example, the virtual model (constructed at 120 with respect to FIG. 1) represents the patient's joint with a given implant configuration. The virtual model can therefore be used to determine a pre-operative plan to implant an implant with the implant configuration into the patient's joint if the calculated post-operative muscle moment capacity and/or determined implant suitability suggest that the implant is suitable. The pre-operative plan may be automatically determined or constructed based on the implant configuration and may be provided to a clinician for surgery.

Muscle Moment Capacity Curves

Estimating post-operative function of a patient's joint using muscle moment capacities can be used to determine whether a given implant configuration is suitable for the patient and will effectively restore post-operative function. In addition to estimating post-operative function of the patient's joint, calculated muscle moment capacities can be used to determine whether a given implant configuration is more suitable than another implant configuration. Furthermore, calculated muscle moment capacities can be used to optimise or ameliorate characteristics of the implant configuration.

FIG. 7 depicts a method of determining a configuration of an implant. A virtual model of at least part of a patient's joint and associated musculature is constructed at 710. The virtual model can be based at least partially on patient-specific data which may optionally be received at 720. The virtual model is also based at least partially on one or more implant configurations. The implant configuration can comprise information about the implant itself (such as its type, geometry, and size), and information describing how the implant is oriented or arranged within the virtual model (e.g. its position and inclination/attitude). A single implant configuration may be assessed or optimised, or multiple implant configurations may be assessed and potentially compared against one another.

A muscle moment capacity curve is then estimated for each of the one or more implant configurations at 730 using the virtual model of at least part of the patient's joint. The muscle moment capacity curve(s) estimated at 730 shows the capacity of the muscles to produce moments at different points in a range of motion of the joint. An implant configuration is then selected at 740 based at least partially on the estimated muscle moment capacity curve(s) that are determined at 730.

The muscle moment capacity curve(s) that is/are estimated at 730 can be determined by calculating the muscle moment capacity of one or more muscles as the virtual model of the patient's joint moves through a simulated range of motion. For example, the virtual model may be a model of a patient's hip and may be simulated through a gait cycle.

The muscle moment capacity of the muscles involved in the gait cycle can be computed at each point in the gait cycle as has been described herein. The calculated muscle moment capacity of the muscles can then be graphed on a muscle moment capacity curve against different points in the gait cycle. This can help clinicians determine the impact of an implant configuration for the patient. A net joint capacity curve for the joint can also be estimated and displayed.

In some examples, the muscle moment capacity at a given point in a range of motion can be calculated by simulating motion of the virtual model of the patient's joint, computing the maximum (or fully activated) isometric force given the musculotendon length at points in the gait cycle, and by computing the moment arm of the muscle at the same points in the gait cycle. In other examples, the calculation may not assume isometric contractions, and a more sophisticated approach can be taken where the specific kinds of muscle contractions used in the range of motion are also simulated. Furthermore, if patient-specific data for muscle activation is known, then an isometric force may be calculated using that patient-specific data rather than assuming maximum activation.

The different ranges of motion used to determine the muscle moment capacity curve(s) at 730 can depend on the implant configuration and the patient's joint. In some examples, the range of motion can comprise a flexion, abduction, or rotation about a joint, and the muscle moment capacities can be calculated at different joint angles to determine the curve. In these examples, the x-axis of the muscle moment capacity curve(s) can be expressed as an angle of flexion, abduction, or rotation. In other examples, the range of motion may be a functional task or movement (some examples of which have been previously mentioned), and the x-axis of the muscle moment capacity curve can be expressed as a percentage of the functional movement. In some examples, each joint may have multiple (e.g. 3) range of motion curves corresponding to rotation about different axes. In other examples, a single curve representing a combined motion can be used. The range of motion used to simulate movement of the virtual model can be determined using a library of reference motions or generic motions that can be used as references to calculate muscle moment capacity curves. In other examples, patient-specific data (acquired by e.g. motion capture) can be used to simulate movement of the virtual model of the patient's joint.

Figure 8:
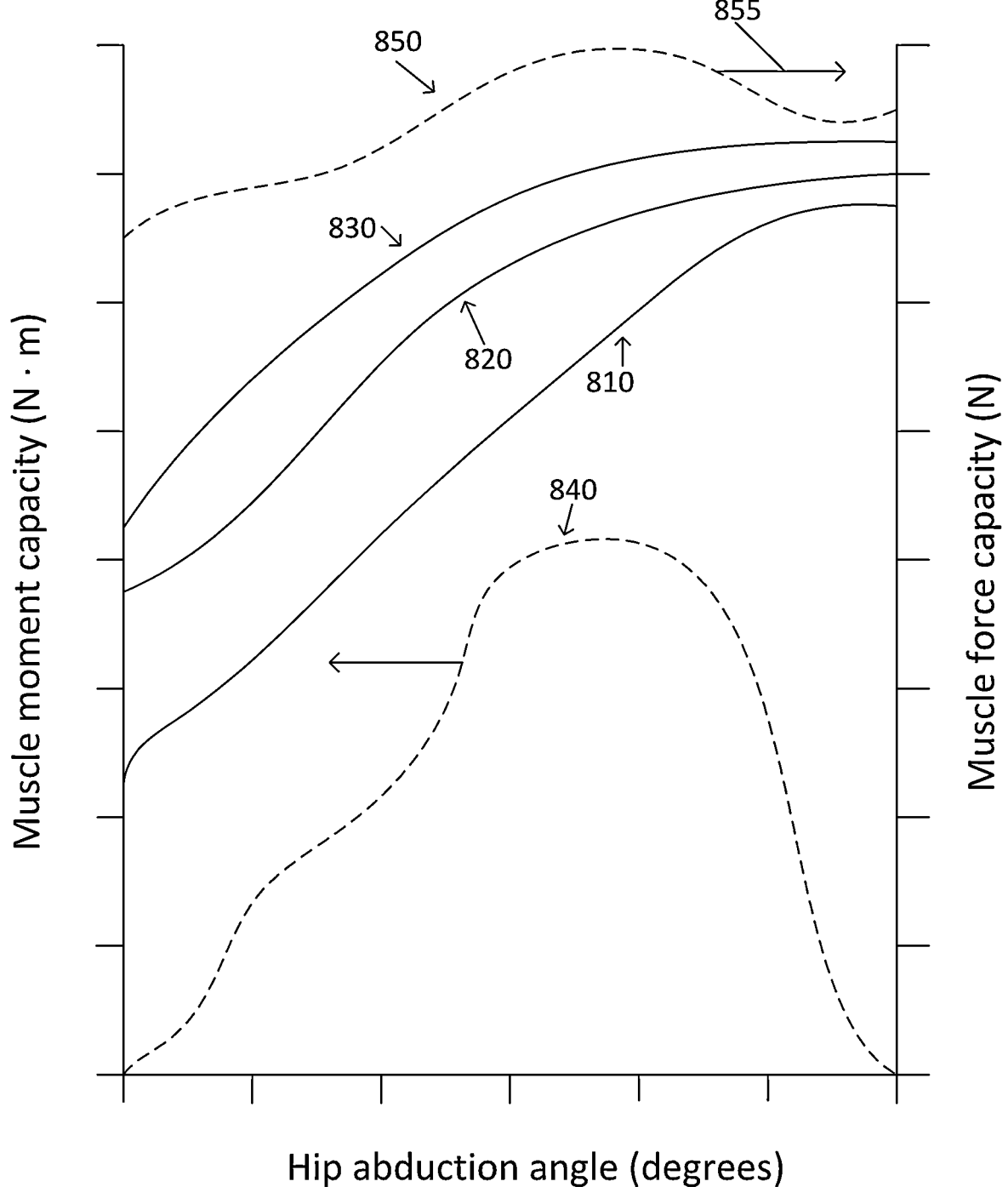
FIG. 8 depicts example muscle moment capacity curves.

FIG. 8 illustrates an example graph showing a plurality of muscle moment capacity curves 810, 820, and 830. This graph can be displayed on a user interface (using e.g. a computer monitor) for a clinician to evaluate pre-operatively, intra-operatively, or post-operatively. In this example, each curve 810-830 represents moment capacities of the hip adductor against hip abduction angle. Each muscle moment capacity curve 810-830 corresponds to a different implant configuration (upon which the virtual model of the patient's joint is at least partially based.) It can be seen that the implant configuration corresponding to curve 830 leads to an increased moment capacity compared to the other muscle moment capacity curves 810 and 820.

The example graph 800 also includes a limit 840 in the form of a lower threshold. This threshold corresponds to an insufficient muscle moment capacity for the muscle or muscle group to move the joint through its range of motion and can be equivalent to 620 with respect to FIG. 6. In some examples, a plurality of limits can be implemented into the muscle moment capacity curve, with each limit corresponding to an implant configuration. This can reflect situations where the geometry introduced by an implant configuration not only affects the muscle moment capacity of the patient's joint, but also affects the muscle moment capacities required to move the joint through its range of motion or its functional task. The limit 840 can be calculated using, for example, the methods described with respect to 620 of FIG. 6, and the limit may be scaled as a function of the patient's height and mass.

If a muscle moment capacity curve dips below the limit 840 (or its corresponding limit if multiple limits are used), then the implant configuration corresponding to that muscle moment capacity curve may cause the muscles or muscle groups to lack the required force or moment capacity to move the joint through its range of motion or functional task. The limit 840 can be used to determine if a given implant configuration is compatible with the patient or to determine which implant configuration should be selected at 740 with respect to FIG. 7 (for example, by maximising the distance between the limit 840 and the muscle moment capacity curves 810-830.) Other muscle moment capacities curves may not include limits or lower thresholds.

The muscle moment capacity curve illustrated in FIG. 8 also includes a limit 850 in the form of an upper threshold. This threshold can correspond to an excessive muscle force capacity and can be equivalent to the upper threshold 630 with respect to FIG. 6 and may be calculated or estimated using the same techniques. In some examples, the upper threshold may be expressed in terms of muscle moment capacities or may be mapped against a second y-axis representing muscle force capacity, indicated by arrow 855. The muscle force capacity used to calculate the muscle moment capacity on the muscle moment capacity curve 810-830 can also be displayed on this axis for comparison with the upper threshold 850. A comparison between the muscle moment capacity curves and upper threshold 850 can be used to help select an implant configuration.

In other examples, additional or alternative upper or lower thresholds can also be calculated and plotted against the muscle moment capacity curve(s). For example, upper thresholds and lower thresholds corresponding to excessive/insufficient joint contact forces (corresponding to 640 with respect to FIG. 6) can be mapped against the muscle moment capacity curve in the appropriate units or on appropriate axes. Similarly, thresholds corresponding to implant-on-implant forces (equivalent to 660 and 670 with respect to FIG. 6) can be calculated and mapped against the muscle moment capacity curve and used to determine or select a given implant configuration at 740 with respect to FIG. 7.

Figure 9:
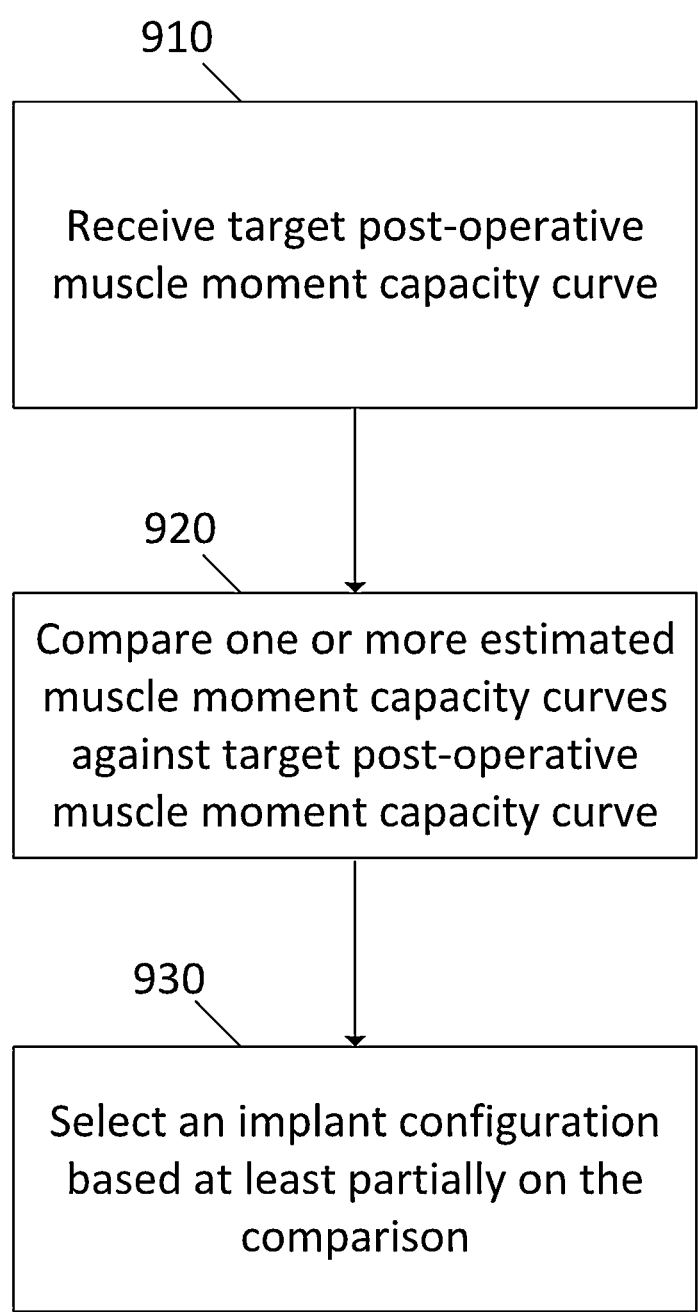
FIG. 9 depicts an example of a use of a target post-operative muscle moment capacity curve.

In some examples, a target post-operative muscle moment capacity curve can be used to help select an implant configuration. FIG. 9 depicts an example approach of using a target post-operative muscle moment capacity curve to aid implant configuration selection. A target post-operative muscle moment capacity curve is received at 910. One or more estimated muscle moment capacity curves (which may be e.g. produced at 730 with respect to FIG. 7) are compared against the target post-operative muscle moment capacity curve at 920. An implant configuration is then selected at 930 based at least partially on the comparison at 920.

In some examples, the target post-operative muscle moment capacity curve received at 910 can represent an ideal curve that an implant configuration aims to achieves. The target post-operative muscle moment capacity curve can then serve as a reference curve used to select implant configurations at 930.

In some examples, the target post-operative muscle moment capacity curve is based at least partially on a pre-operative muscle moment capacity curve, which may be calculated using a pre-operative virtual model of a patient's joint or may be estimated through patient-specific data (for example, kinematic measurements and motion capture of the patient.) The target post-operative muscle moment capacity curve may be proportional to the pre-operative muscle moment capacity curve. For example, the target post-operative muscle moment capacity curve may be scaled from the pre-operative muscle moment capacity curve, such as 120% of the pre-operative muscle moment capacity curve. Alternatively, only some portions of the pre-operative muscle moment capacity curve may be scaled if an implant configuration is needed to only address some particular weakness in the muscle moment capacity. In still further examples, the target muscle moment capacity curve received at 910 may be at least partially user defined. For example, a clinician may manually determine at least a part of the target muscle moment capacity curve to achieve a patient-specific outcome.

In some examples, the selection of an implant configuration at 930 is at least partially based on a difference between the muscle moment capacity curve associated with that implant configuration and the target post-operative muscle moment capacity curve. For example, the selected implant configuration may minimise a difference between an estimated muscle moment capacity curve and the target post-operative muscle moment capacity curve. The selection of an implant configuration may also be based at least partially on other factors, such as limits and/or thresholds as have been described.

Figure 10:
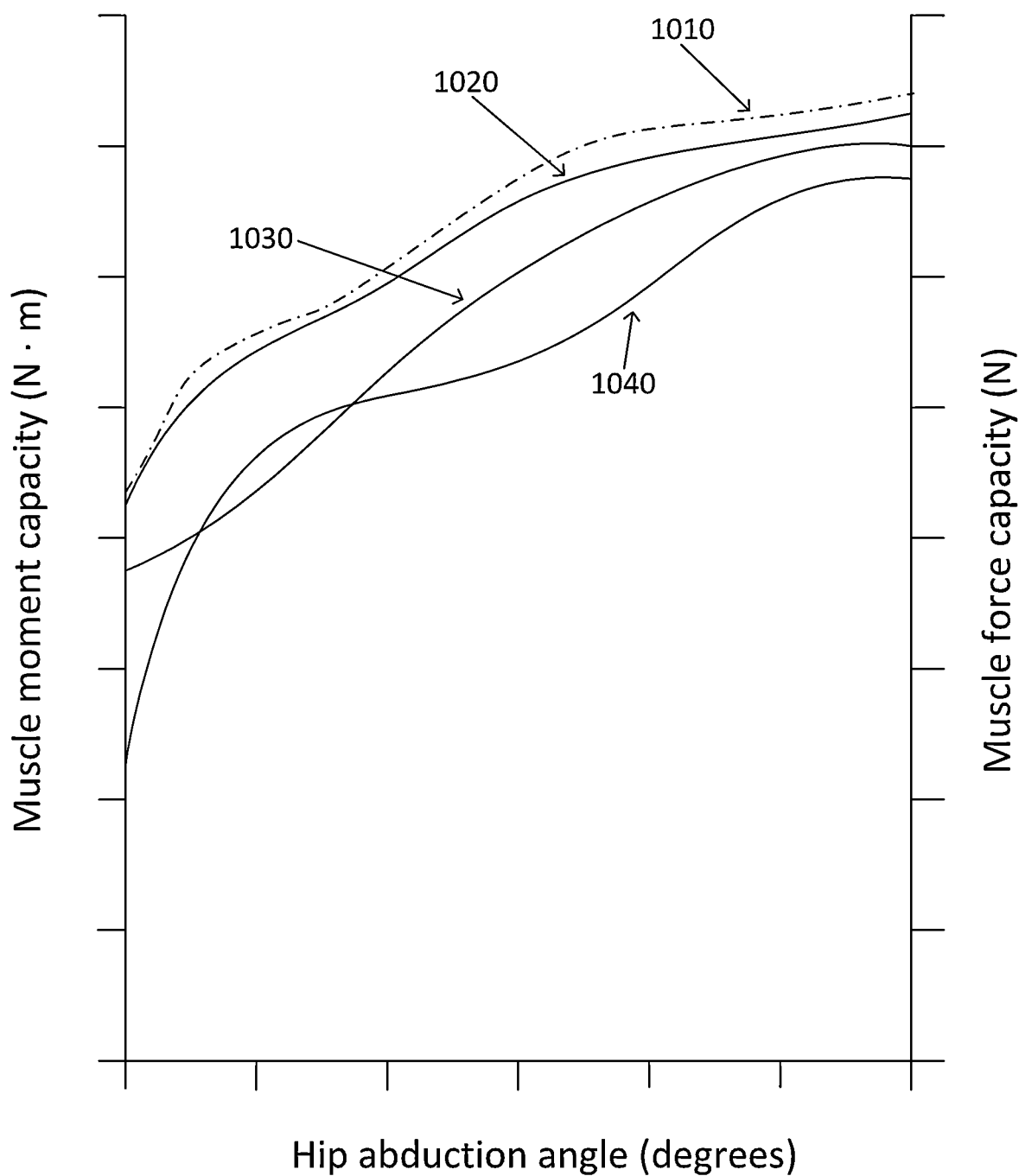
FIG. 10 depicts an example of a target post-operative muscle moment capacity curve.

FIG. 10 depicts an example of a target post-operative muscle moment capacity curve 1010. The target post-operative muscle moment capacity curve 1010 is displayed alongside a series of estimated muscle moment capacity curves 1020, 1030, and 1040 that correspond to implant configurations. The muscle moment capacity curve 1020 is the closest to the target post-operative muscle moment capacity curve 1010 and therefore may be selected.

The techniques described so far can be used to assess different implant configurations against one another, such as different types or locations of otherwise equivalent implants. However, these techniques and muscle moment capacity curves can also be used to optimise a given implant configuration or to design an implant configuration.

For example, a given implant configuration can comprise information about the implant itself (such as its type, geometry, and size), and information describing how the implant is oriented or arranged within the virtual model (e.g. its position and inclination/attitude). To optimise or ameliorate the implant configuration, a number of the properties of the implant configuration may be fixed (such as its type or size) while other properties (such as an acetabular cup angle) can be varied to create a plurality of implant configurations. For each variation, a virtual model of the patient's joint can be modified or constructed and a muscle moment capacity curve can be determined for the corresponding implant configuration. Each muscle moment capacity curve can then be compared against a target post-operative muscle moment capacity curve and scored depending on a difference between the curve and the target curve. This process can iterate until an implant configuration that best fits the target muscle moment capacity curve is determined. Other properties of the implant configuration can also be iteratively varied and assessed in the same way to determine an implant configuration that fits the target post-operative muscle moment capacity curve. In this way, an implant configuration can be optimised or designed for a specific patient and their target post-operative muscle moment capacity.

For example, a patient may present to a clinician requiring a certain implant, such as a hip implant. The clinician can take pre-operative measurements of the patient to determine patient-specific data and can determine a pre-operative muscle moment capacity curve for the patient. The clinician can then produce a target post-operative muscle moment capacity curve for the patient which addresses patient-specific weaknesses in the patient's muscle moment capacity. The clinician can construct a virtual model of the patient's joint using patient-specific data and can initially begin with an implant configuration that they believe will address the patient's needs. The post-operative function of the patient's joint can be estimated by calculating a muscle moment capacity using the virtual model of the patient's joint and determining a muscle moment capacity curve. The muscle moment capacity curve can then be compared against the target post-operative muscle moment capacity curve and the configuration of the implant can be iteratively changed to determine an implant configuration that minimises a difference between the muscle moment capacity curve and target post-operative muscle moment capacity curve, whilst staying within any limits or thresholds (e.g. corresponding to an insufficient force) that may be defined. When the appropriate implant configuration has been determined, the clinician can be presented with a pre-operative and patient-specific plan for the patient.

Muscle moment capacity curves and target post-operative muscle moment capacity curves can also be used to inform post-operative rehabilitation of the patient. After an implant configuration is confirmed (which may be done via post-operative imaging), muscle moment capacity curves can be calculated and a change from the patient's pre-operative state can be determined. This information can be used to determine which muscles should be exercised more during post-operative rehabilitation and what exercises may be used. For example, muscles which have a significantly decreased moment capacity after surgery may be specifically targeted for extra training to improve post-operative function. For example, hip abductors are needed during the single stance phase of walking to maintain the correct hip posture. If the cup placement is lateralised during surgery, the moment arm of the muscles may be reduced alongside their capacity to provide hip abduction. The consequence of this is often seen in terms of altered movement patterns as a compensation. These may be specifically identified and addressed in post-surgical rehabilitation.

The methods discussed herein can be performed pre-operatively, intra-operatively, or post-operatively. Pre-operative approaches can be used to assess implants for pre-operative planning and to estimate post-operative functions of joints. Intra-operative approaches can be used, for example, to determine the effect of planned procedure components (e.g. planned implants) based on one or more other components (e.g. another implant) that have already been delivered. Similarly, parameters of planned procedure components (e.g. implants) can be optimised given the fixed parameters of one or more already delivered components (e.g. implants). Performing one or more of the disclosed methods pre-operatively can help select better or optimal implant(s) and/or implant parameters to achieve a patient-specific outcome. Performing one or more of the disclosed methods intra-operatively can help select better or optimal implant(s) and/or implant parameters based on an already-delivered implant or already-planned parameters. Performing a method intra-operatively on a set of already-delivered implants can allows the clinician to update predicted post-operative function during the surgery if the clinician decides to use different implants, resect the bone differently, or find additional constraints. It also gives the clinician up-to-date information during the surgery.

When performing a method post-operatively on a set of already-delivered implants, the methods can provide an updated post-operative function prediction. This can then be used by the surgeon to manage expectations for the patient and be used in physiotherapy as guidelines for expected function. The methods can also give the surgeon feedback on how their plan and execution may differ, and improve the model parameter estimation algorithms and the forward simulation algorithm by comparing actual to estimated post-operative posture.

The methods and programs described herein can allow simulation of the outcome of a surgical procedure without the need to perform it, improve accuracy of a simulation of a joint, reduce computational complexity of virtual models of a joint, facilitate optimisation of a parameter of a surgical procedure, and/or facilitate selection of an appropriate implant or resection for a subject.

The computing device used to construct the virtual model, host the image sub-system, and used to execute the methods disclosed herein may comprise an electronic computing device. For example, the electronic computing device may be a tablet, a phone, a personal computer, a server, or a similar device. The electronic computing device may be a single computer, a single server, or have the functionality performed by a server apparatus distributed across multiple server components connected via a communications network (either a private LNA, WAN or public internet). The computer or server apparatus may include a number of individual components including, but not limited to, one or more microprocessors, a memory (e.g. a volatile memory such as a RAM) for the loading of executable instructions, the executable instructions defining the functionality the server apparatus carries out under control of the processor. There may also be an input/output module allowing the server to communicate over a communications network. A user interface can be provided for user control and may comprise, for example, computing peripheral devices such as display monitors, computer keyboards and the like. Server apparatus also comprises a database, for storing patient specific data, statistical anatomical data, and models for various available implants.

The methods may be executed through software stored on non-transitory media that can run on any suitable device. In some examples, the software may be stored on a non-transitory computer-readable storage medium having instructions stored thereon that, when executed by one or more processors of a first computing device, performs a method of estimating post-operative function of a patient's joint, the method comprising: receiving patient-specific data for the patient's joint, constructing a virtual model of at least part of the patient's joint and associated musculature, wherein the virtual model is based at least partially on the patient-specific data and an implant configuration, and calculating a post-operative muscle moment capacity for the patient's joint based at least partially on the virtual model.

In some examples, software may be stored on a non-transitory computer-readable storage medium having instructions stored thereon that, when executed by one or more processors of a first computing device, performs a method of determining a configuration of an implant, the method comprising: constructing a virtual model of at least part of a patient's joint and associated musculature, wherein the virtual model is based at least partially on one or more implant configurations, for each of the one or more implant configurations, estimating a muscle moment capacity curve over a range of motion using the virtual model, and selecting an implant configuration based at least partially on the estimated muscle moment capacity curve(s).

In some examples, memory storing data instructions can be executed on at least one processor that is part of a system to cause the processor to perform the method. For example, a system can comprise at least one processor and memory storing data instructions that when executed by the at least one processor cause the at least one processor to: receive patient-specific data for a patient's joint; construct a virtual model of at least part of the patient's joint and associated musculature, the virtual model based at least partially on the patient-specific data and an implant configuration; and calculate a post-operative muscle moment capacity for the patient's joint based at least partially on the virtual model.

In still further examples, a system can comprise at least one processor; and memory storing data instructions that when executed by the at least one processor cause the at least one processor to: construct a virtual model of at least part of a patient's joint and associated musculature, wherein the virtual model is based at least partially on one or more implant configurations; for each of the one or more implant configurations, estimate a muscle moment capacity curve over a range of motion using the virtual model; and select an implant configuration based at least partially on the estimated muscle moment capacity curve(s).

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

What is claimed is:

1. A method of generating a patient-specific surgical plan for a patient's joint, the method comprising:
   receiving patient-specific radiological data for the patient's joint, segmenting the radiological data via a processor to construct a 3D musculoskeletal model;
   calculating a post-operative muscle moment capacity over a target range of motion defined by a physiological task;
   optimizing a 3D coordinate position of an implant configuration by iteratively adjusting the 3D coordinate position within the 3D musculoskeletal model until the calculated post-operative muscle moment capacity meets a target physiological threshold; and
   outputting a surgical plan comprising the optimized 3D coordinate position for the implant configuration.

2. The method of claim 1, wherein the patient-specific radiological data comprises muscle data, bone data, or tendon data.

3. The method of claim 1, wherein the 3D musculoskeletal model comprises a volumetric representation of a muscle.

4. The method of claim 3, wherein calculating the post-operative muscle moment capacity comprises simulating a change in muscle fibre length as a function of joint angle.

5. The method of claim 1, wherein the method further comprises calculating a post-operative net joint capacity based at least partially on the post-operative muscle moment capacity.

6. The method of claim 1, wherein the method further comprises calculating a joint contact force.

7. The method of claim 1, wherein the method further comprises determining an implant-on-implant contact force.

8. The method of claim 1, wherein the method further comprises outputting a suitability score for the implant configuration based at least partially on the calculated post-operative muscle moment capacity.

9. The method of claim 1, wherein the method further comprises providing an implant recommendation based at least partially on the calculated post-operative muscle moment capacity.

10. The method of claim 1, wherein the method further comprises generating a post-operative rehabilitation plan by mapping the optimized muscle moment capacity to a set of physical therapy exercises designed to strengthen specific muscle groups identified as having sub-optimal capacity in the 3D musculoskeletal model.

11. A system comprising:

at least one processor; and memory storing data instructions that when executed by the at least one processor cause the at least one processor to:

receive patient-specific radiological data for a patient's joint;

calculate a post-operative muscle moment capacity over a target range of motion defined by a physiological task;

optimize a 3D coordinate position of an implant configuration by iteratively adjusting the 3D coordinate position within a 3D musculoskeletal model until the calculated post-operative muscle moment capacity meets a target physiological threshold; and output a surgical plan comprising the optimized 3D coordinate position for the implant configuration.

12. The system of claim 11, wherein the patient-specific radiological data comprises muscle data, bone data, or tendon data.

13. The system of claim 11, wherein the 3D musculoskeletal model comprises a volumetric representation of a muscle.

14. The system of claim 13, wherein calculating the post-operative muscle moment capacity comprises simulating a change in muscle fibre length as a function of joint angle.

15. The system of claim 11, wherein the processor is further configured to calculate a post-operative net joint capacity based at least partially on the post-operative muscle moment capacity.

16. The system of claim 11, wherein the processor is further configured to calculate a joint contact force.

17. The system of claim 11, wherein the processor is further configured to determine an implant-on-implant contact force.

18. The system of claim 11, wherein the processor is further configured to output a suitability score for the implant configuration based at least partially on the calculated post-operative muscle moment capacity.

19. The system of claim 11, wherein the processor is further configured to output an implant recommendation based at least partially on the calculated post-operative muscle moment capacity.

20. The system of claim 11, wherein the processor is further configured to generate a post-operative rehabilitation plan by mapping the optimized muscle moment capacity to a set of physical therapy exercises designed to strengthen specific muscle groups identified as having sub-optimal capacity in the 3D musculoskeletal model.

* * * * *